United States Patent [19]

Friedman et al.

[11] Patent Number: 5,679,574

[45] Date of Patent: Oct. 21, 1997

[54] QUANTITATIVE TEST FOR OILS, CRUDE OIL, HYDROCARBON, OR OTHER CONTAMINANTS IN SOIL AND A KIT FOR PERFORMING THE SAME

[75] Inventors: Stephen B. Friedman, Chapel Hill; Thomas N. Stewart; Patrick Mize, both of Durham, all of N.C.

[73] Assignee: Ensys Environmental Products, Inc., Morrisville, N.C.

[21] Appl. No.: 369,805

[22] Filed: Jan. 9, 1995

[51] Int. Cl.[6] .................................................. G01N 33/24
[52] U.S. Cl. .......................... 436/29; 436/25; 436/27; 436/30; 436/40; 436/139; 422/68.1
[58] Field of Search .......................... 436/25, 27, 28–31, 436/40, 60, 139, 20, 22, 23; 422/61, 68.1, 99, 101; 73/61.43, 61.44, 153, 155, 863.12, 866

[56] References Cited

U.S. PATENT DOCUMENTS

| | | | |
|---|---|---|---|
| 2,767,320 | 10/1956 | Coggeshall et al. | 436/29 X |
| 2,800,460 | 7/1957 | Grosskopf et al. | 436/139 |
| 2,951,940 | 9/1960 | Graham et al. | 436/30 X |
| 3,303,002 | 2/1967 | McAuliffe | 436/30 |
| 3,746,511 | 7/1973 | Stookey et al. | 23/231 |
| 3,775,059 | 11/1973 | Hearn | 436/139 |
| 3,960,493 | 6/1976 | Beitz et al. | 23/230 B |
| 4,056,969 | 11/1977 | Barringer | 73/28 |
| 4,343,897 | 8/1982 | Neumann et al. | 435/19 |
| 4,755,469 | 7/1988 | Showalter et al. | 436/27 |
| 4,792,526 | 12/1988 | Ouellette et al. | 436/29 |
| 4,980,295 | 12/1990 | Udy | 436/21 |
| 5,155,546 | 10/1992 | Balsam et al. | 356/300 |
| 5,181,428 | 1/1993 | Chriswell | 73/863.12 |
| 5,351,532 | 10/1994 | Hager | 73/153 |

OTHER PUBLICATIONS

Zhang et al, A method for detn. of crude petroleum oil in soil using tetrahydrofuran–turbidimetric method, 1988, Huanjing Kexue Journal, Abstract, 9(4), 57–8,52.

*Primary Examiner*—Harold Pyon
*Attorney, Agent, or Firm*—Oblon, Spivak, McClelland, Maier & Neustadt, P.C.

[57] ABSTRACT

A method for the quantitative determination of oil in a soil matrix is provided, in which the method involves: extracting a soil sample with a solvent in the presence of a drying agent to provide an extract containing oil, if present in the soil sample, wherein the solvent is capable of complete solvation of oil and is completely miscible with water; filtering the extract; combining the filtered extract with water in the presence of an emulsifier to form an assay sample; and determining the amount of oil in the soil sample by measuring the turbidity of the assay sample to provide a turbidimetric response for the assay sample which correlates to concentration of oil present in the assay sample and comparing the turbidimetric response to a standard curve prepared from performing the methods on soil samples of known oil content. A kit for performing the method is also provided.

18 Claims, 2 Drawing Sheets

QUANTITATIVE TEST FOR OILS, CRUDE OIL, HYDROCARBON, OR OTHER CONTAMINANTS IN SOIL AND A KIT FOR PERFORMING THE SAME

BACKGROUND OF THE INVENTION

1. Field of the Invention

The present invention relates to methods for the quantitative detection of hydrophobic contaminants in soil, especially oils, crude oil and hydrocarbon contaminants, and a kit for performing the method.

2. Description of the Background

In testing soil for the presence of oils, such as crude oil, it is necessary to have a reliable test which meets regulatory standards imposed by the Environmental Protection Agency. The current standard method for quantitation of oil is EPA method 9071. However, this particular method requires the use of trichlorofluoroethane (Fluorocarbon 113) in order to perform the step of extraction of the oil or grease from the dried sludge sample. With the recent crackdown on the use of chlorofluorocarbons (CFCs), this method is thus coming under scrutiny, with a great desire to find a method suitable for quantitation of oils in soil or sludge samples which is more environmentally palatable.

Chriswell, U.S. Pat. No. 5,181,428 discloses a method for testing soil samples wherein the soil sample is placed in a soil sample filter container and washed with butane. Upon evaporation of the butane wash, the non-volatile residue is analyzed by gas chromatography for the presence of hydrocarbons. However, such a method requires the evaporation of volatile and potentially harmful solvents and other volatile contaminants. Further, such a method requires the use of a gas chromatograph, a rather bulky piece of laboratory equipment which is difficult to use at a soil remediation site.

Balsam et al, U.S. Pat. No. 5,155,546 pertains to a method of detecting organic materials in rocks and sediments using visible light spectra. This method uses the reflectance spectral data from a rock and/or sediment sample to quantitatively determine the presence of organic carbon. However, once again, expensive reflectance spectrometers are required to perform such a method.

Campbell, et al, U.S. Pat. No. 2,367,664 discloses a method of petroleum exploration which involves extraction of soil samples with a solvent and measuring the fluorescence spectrum of any petroleum oils present to determine their presence in the samples. Once again, a fluorescence spectrometer, an expensive laboratory item, is required.

A quick and simple method for the quantitative detection of oil, especially crude oil, in a soil matrix is desired for use in soil remediation efforts. Such a method must be simple to perform, use portable, inexpensive equipment, the results must be easy to interpret and the method should avoid the use of environmentally hazardous CFCs and high temperature steps. Such a method would greatly enhance remediation efforts on sites which have been subjected to oil contamination.

SUMMARY OF THE INVENTION

Accordingly, one object of the present invention is to provide a quick and easy method for the quantitation of hydrophobic contaminants in soil matrices.

A further object of the present invention is to provide a method for quantitation of oils, especially crude oil, present in a soil matrix which can be performed rapidly and simply at the location of the contaminated soil, i.e. for remediation of contaminated sites.

A further object of the present invention is to provide a kit for performing the method.

These and other objects of the present invention have been satisfied by the discovery of a method for the quantitation of oil in a soil matrix, comprising:

(a) dispersing a particulate free extract of a dried soil sample suspected of containing crude oil in an aqueous medium, comprising: an emulsifier and water;

(b) measuring the turbidity of the resultant dispersion; and (c) comparing the turbidity to a standard curve to obtain concentration of oil in the soil matrix, and a kit for performing the method.

BRIEF DESCRIPTION OF THE FIGURES

Various other objects, features and attendant advantages of the present invention will be more fully appreciated as the same becomes better understood from the following detailed description when considered in connection with the accompanying figures wherein.

DESCRIPTION OF THE PREFERRED EMBODIMENTS

Figure 1:
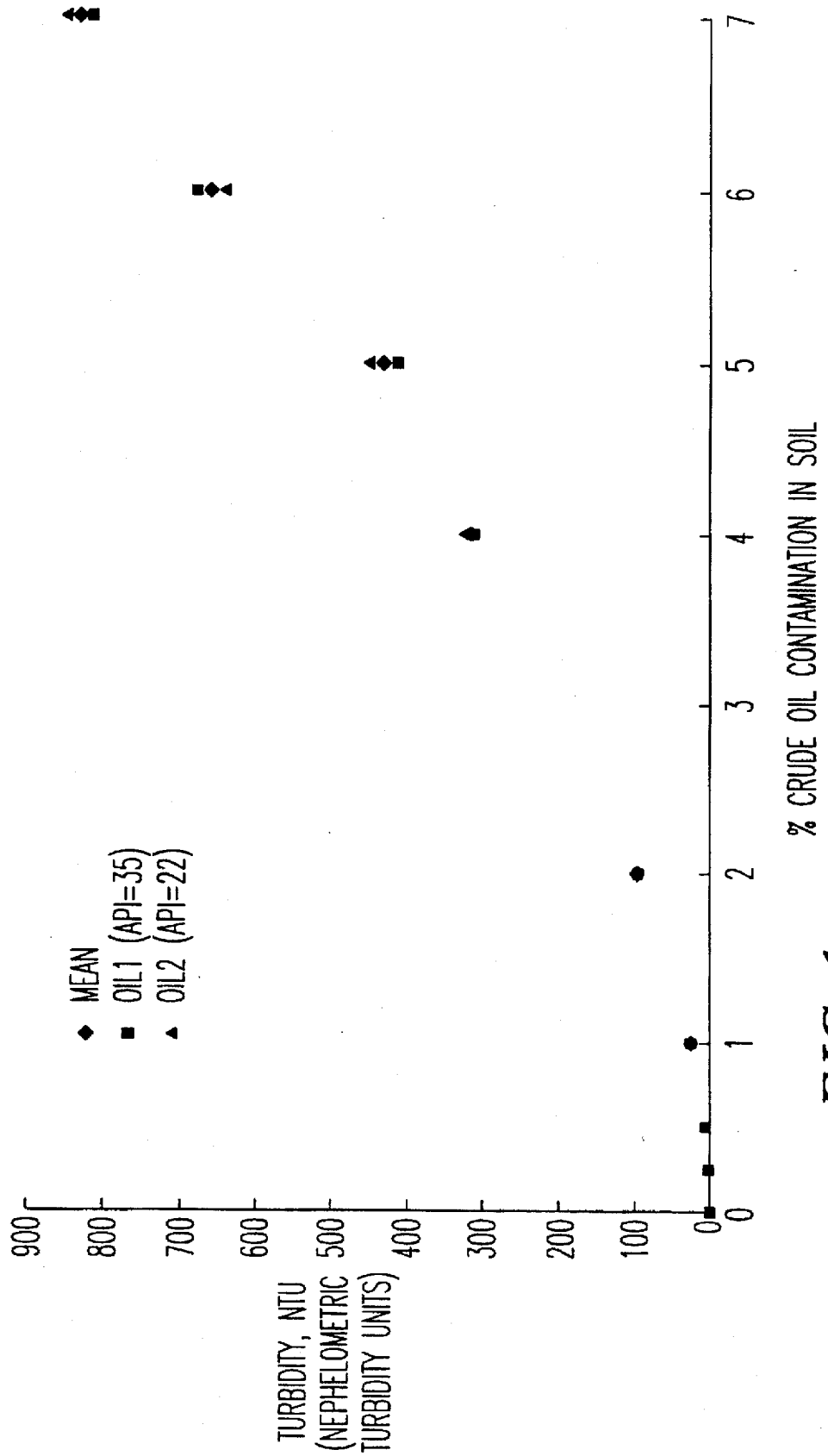
FIG. 1 is a graph showing the response of high and low API (American Petroleum Institute) number oils using the present method.

The present invention relates to a simple method for the guantitation of hydrophobic compounds or mixtures of such compounds, such as crude oils, oils, refined and unrefined petroleum mixtures and other synthetic oils and greases, in soil matrices (hereafter the term oil will be used to mean a hydrophobic mixture or compound).

The present method is based on drying and extraction of a soil matrix with a solvent and drying agent, filtering the solvent extract, and dispersion of the filtered extract in water with a small amount of a surfactant. The resulting mixture forms a stable emulsion when oil is present in the soil matrix sample, with the turbidity of the emulsion being proportional to the original concentration of the oil in the soil matrix. Contamination is quantitated by measuring the reflectance of light from the emulsion formed.

EXTRACTION AND DRYING

Solvent properties are very important for extraction and subsequent emulsion formation in the present invention. The solvent used must have rather unique properties. In particular the solvent must be able to quantitatively extract the oil from a soil matrix. This requires strong solvating power for oil, when the solvent is dry. However, the solvent must also be completely water miscible. This allows the solvent to dissolve in the dilute aqueous surfactant used in the present method and any extracted oil, if present, to disperse forming an emulsion. Suitable solvents for use in the extraction step include the short chain $C_1-C_3$ alcohols, ether alcohols, and ethers. The $C_1-C_3$ short chain alcohols include methanol, ethanol, propanol, and isopropanol. Suitable ether alcohols include 2-methoxyethyl alcohol, 2-ethoxyethyl alcohol, 3-ethoxy propanol, di(ethylene)glycol methylether, di(ethylene)glycol ethyl ether, di(propylene glycol), tri(ethylene glycol) and poly(ethylene glycol)s and diglyme (2-methoxyethyl ether). Of the ethers, preferred solvents include tetrahydrofuran, dioxane, ethyleneglycol dimethyl ether, 1,2-dimethoxy propane, 2-methoxymethylether (diglyme) and 2-ethoxyethyl ether. The most preferred solvent is diglyme. The solvent used is added to the soil suspected of being contaminated, in an amount of from 1 mL/g of soil to 5 mL/g of soil, preferably 1.5–2.5 mL/g of soil, most preferably 2 mL/g of soil.

Drying of the solvent and soil during the extraction phase is crucial for eliminating quantitative errors which may arise from excess water. Soil matrixes typically have a water (wetness) content of 5–40%. This water content of the soil dissolves in the solvent and can reduce its capacity for dissolving the oil contaminant, thus resulting in a false negative reading or negative quantitative bias. Thus it is necessary to provide a drying agent with the ability to absorb large amounts of water by weight, but have minimal affinity for adsorbing the extraction solvent. If the drying agent has too high an affinity for the extraction solvent, the drying agent becomes too difficult to filter.

Suitable drying agents for use in this step include anhydrous $Na_2SO_4$ (sodium sulfate), 4 Å molecular sieves (both rods and 6 uM powder form), anhydrous $MgSO_4$ (magnesium sulfate), anhydrous calcium sulfate, alumina, silica gel, calcium chloride, and phosphorous oxide, with anhydrous magnesium sulfate powder being preferred. When adding the drying agent to the soil/solvent mixture, the drying agent is added in a weight ratio of from 0.5:1 to 1.5:1 of drying agent:wet soil. The extraction time should be a period of from 1 to 5 minutes. There appears to be no significant effect on assay results over this extraction time range. For example 5 g of powdered $MgSO_4$ added to 5 g of a 30% wet soil and 10 mL of diglyme reduces the aqueous percentage of the diglyme from 15 to 3% after 1 minute of shaking. This example illustrates a preferred method for drying and extraction of soil matrices according to the present method.

FILTERING

In order to accomplish the present method, it is necessary to provide a final sample extract which is essentially particulate free. This is accomplished by filtering the extract obtained in the extraction step.

Filtering of the extraction solvent is accomplished by placing the solvent/soil mixture in a suitable filtering means, and pushing the solvent through the filter. Suitable filtering means must provide rapid and easy filtering of the extract from the soil without clogging. Any filter which will readily filter soil from the solvent is acceptable. A preferred filter is a Whatman Uniprep 0.4 µm filter. The filtering step is important since it removes particulate matter which can give false positive readings in the subsequent turbidimetric interpretation and quantitation step.

EMULSION FORMATION

A key concept in the development of the present method was the recognition that emulsions of oils having different compositions provide a relatively uniform quantitative response as measured in turbidity units (see FIG. 1). In forming the emulsions of the present method it is crucial to use an emulsifier which has the following unique properties: 1) the ability to form a stable oil-in-water emulsion with any oil present, 2) no measurable turbidity (NTU<1) when no oil is present, 3) solubility in water at concentrations of up to 0.5%, 4) HLB (hydrophilic/lipophilic balance) number of 9–18, most preferably 12–16, 5) nonionic. If no emulsifier is used, the dilute solution of oil in the extracted solvent may still form an emulsion at low concentration but the turbidity of the water, oil, solvent mixture can actually decrease with increasing oil concentration providing a limited range and a non-proportional response, as well as an emulsion which is not stable.

Suitable emulsifiers for use in this step include Triton X-100 (HLB 13.5) alkylphenoxy polyethoxy ethanol, Triton X-102 (HLB 14.6) octylphenoxy polyethoxy ethanol, Triton X-114 (HLB 12.4) octylphenoxy polyethoxy ethanol, Triton X-45 (HLB 10.4) octylphenoxy polyethoxy ethanol, Triton X-165 (HLB 15.8) octylphenoxy polyethoxy ethanol, Tween 20 (HLB 16.7) POE (20) sorbitan monolaurate, Tween 21 (HLB 13.3) POE (4) sorbitan monolaurate, Tween 60 (HLB 14.9); POE (20) sorbitan monostearate, and Rhodasurf LA 90 (HLB 13.5) Linear synthetic alcohol ethoxylate, with Triton X-100 being preferred.

The concentration of emulsifier used is an amount sufficient to provide emulsion, and up to 0.5%. Preferably, the emulsifier is used at an amount of from 0.03 to 0.1%, with 0.05% being most preferred in the case of Triton X-100. Triton X-100 at 0.05% provides an absorption response which is linearly proportional to the amount of oil originally present in the soil sample and is highly reproducible. A preferred emulsifying procedure is to pipette 250 uL of the extract into a vial and adding 3.0 mL of the aqueous emulsifying solution to the extract. The mixture is capped and swirled for at least 5 seconds. The resulting mixture is then placed into a disposable glass cuvette for quantitation as described below.

QUANTITATION

Quantitation is accomplished by determining the turbidity of the resulting emulsion in nephalometric turbidity units (NTU) using a simple turbidimeter and comparing that turbidity measurement to a standard curve as shown in FIG. 1. The standard curve provides a correlation between concentration of oil in the soil sample and the NTU turbidity measurement. This correlation follows the equation: $NTU = 29 \times (\% \text{ oil})^{1.75}$.

In the context of the present invention, the response seen is described as turbidity, although it is not known whether the phenomenon is truly one of changing turbidity, (i.e., caused by functionality in the various oil compounds absorbing the particular wavelength of light) or if the phenomenon is merely a change in transmittance due to a variety of factors, such as absorbance, reflection, refraction, etc. Accordingly, the present description uses the term turbidity to merely describe the response seen in measured solution turbidity, without attempting to distinguish between these two possibilities.

In order to provide guantitation by the turbidimetric response, it is necessary to use a conventional calibrated turbidimeter.

An additional embodiment of the present invention is a kit for performing the method of the present invention. The kit of the present invention comprises a solvent for performing the extraction, a drying agent, a means for filtering the extract from the soil sample and an emulsifier. Each of the individual components have been described above with respect to the method of the present invention. In the kit of the present invention, the various components are preferably contained in separate containers to be measured or weighed out as needed for use. Suitable containers must be compatible with the particular component contained therein and are preferably made of such materials as glass or plastic. Optionally included within the kit of the present invention are a turbidimeter and glass cuvette for containing the sample for turbidity measurement. Other optional components include sealable mixing and shaking vessels for preparing the emulsion and weighing boats for measuring out the soil and drying agent.

While it is relatively easy to prepare a standard calibration curve of NTU vs. concentration of oil using standard samples of known oil content, it is most preferred that the kit include a standard curve covering the range of concentrations from 0.25% to 7%, which is the range of most interest in soil remediation work.

The present method has been found to be highly reproducible, showing minimal matrix effects, low variance between test operators, low temperature effects and low lot to lot variance. The method can be performed at temperatures from 4°–40° C. without significant effects on the results.

Having generally described the present invention, a further understanding can be obtained by reference to certain specific examples which are provided herein for purposes of illustration only and are not intended to be limiting of the present invention unless otherwise noted.

EXAMPLES

As an example of the present concept, various crude oils, having different API numbers, were spiked into diglyme at concentrations which mimicked the concentrations that would be observed in soil matrices contaminated at levels between 0.25% and 7%. 250 uL of the spiked diglyme was dispersed in 10.0 mL of 0.05% aqueous Triton X-100. The resulting emulsions gave a predictable turbidimetric response as seen in Table 1 and FIG. 1.

TABLE 1

RESPONSE OF CRUDE OILS IN CRUDE OIL ASSAY OF THE PRESENT INVENTION

| % OIL | OIL1 (API = 35) | OIL 2 (API = 22) | MEAN |
| --- | --- | --- | --- |
| 0 | 0.5 | 0.5 | 0.5 |
| 0.25 | 1.1 | 1.0 | 1.0 |
| 0.5 | 4.4 | 4.7 | 4.5 |
| 1 | 23.9 | 27.7 | 25.8 |
| 2 | 93.4 | 97.9 | 95.6 |
| 4 | 306.5 | 324.5 | 315.5 |
| 5 | 410.0 | 456.5 | 433.3 |
| 6 | 681.5 | 633.0 | 657.3 |
| 7 | 819.0 | 857.0 | 838.0 |

Performing the soil assay for crude oil 5 g of crude oil-contaminated soil were weighed into a weight boat and placed in an extraction vial containing 3.5 g of $MgSO_4$. 20 mL of diglyme were then added to the soil and the resulting mixture shaken for 1 minute and allowed to settle.

1–2 mL of the resulting diglyme extract were then placed in a Whatman Uniprep 0.4 μm filter and filtered to remove particulate matter. 250 uL of the filtered extract were added to a tube along with 10 mL of a 0.05% aqueous solution of Triton X-100. The tube was capped and swirled for 5 seconds, to result in an emulsion if sufficient oil contamination was present.

The resulting liquid was placed in a glass cuvette and the turbidity measured on a turbidimeter in NTU units.

Using this method, samples can be processed and quantitated at a rate of 1 every 5 minutes or 20/hour. Using this method, 18 positive soil matrixes supplied by Exxon were examined for crude oil content. The results are shown in TABLE 2.

TABLE 2

CORRELATION OF SPIKED SAMPLES OF BY METHOD 9071 AND ENSYS CRUDE CHECK ASSAY

| SAMPLE NUMBER | METHOD 9071 RESULTS (% CRUDE) | ENSYS CRUDE CHECK (% CRUDE) |
| --- | --- | --- |
| A1X | 1.3 | 1.3 |
| A2X | 1.4 | 1.3 |
| A3X | 1.8 | 1.4 |
| A1Y | 2 | 2.1 |
| A2Y | 2.7 | 2.7 |
| A3Y | 3.4 | 2.8 |
| A1Z | 3.4 | 3.6 |
| A2Z | 3.1 | 3.5 |
| A3Z | 4.8 | 4.4 |
| B1X | 2.1 | 2.2 |
| B2X | 2 | 2.3 |
| B3X | 2.1 | 2.1 |
| B1Y | 3.6 | 4 |
| B2Y | 3.7 | 4.1 |
| B1Z | 5 | 5.9 |
| B2Z | 4.7 | 5.1 |
| C1X | 2.1 | 2.3 |
| C1Y | 4 | 4.4 |
| C1Z | 5.8 | 6 |
| STANDARD ERROR OF ESTIMATE | | 0.35 |

Values for the turbidimetric measurements are reported along with gravimetric values obtained for these samples using the conventional gravimetric analysis method, EPA method 9071. This turbidimetric interpretive value was derived from the standard curve generated for crude oils depicted in FIG. 1.

Figure 2:
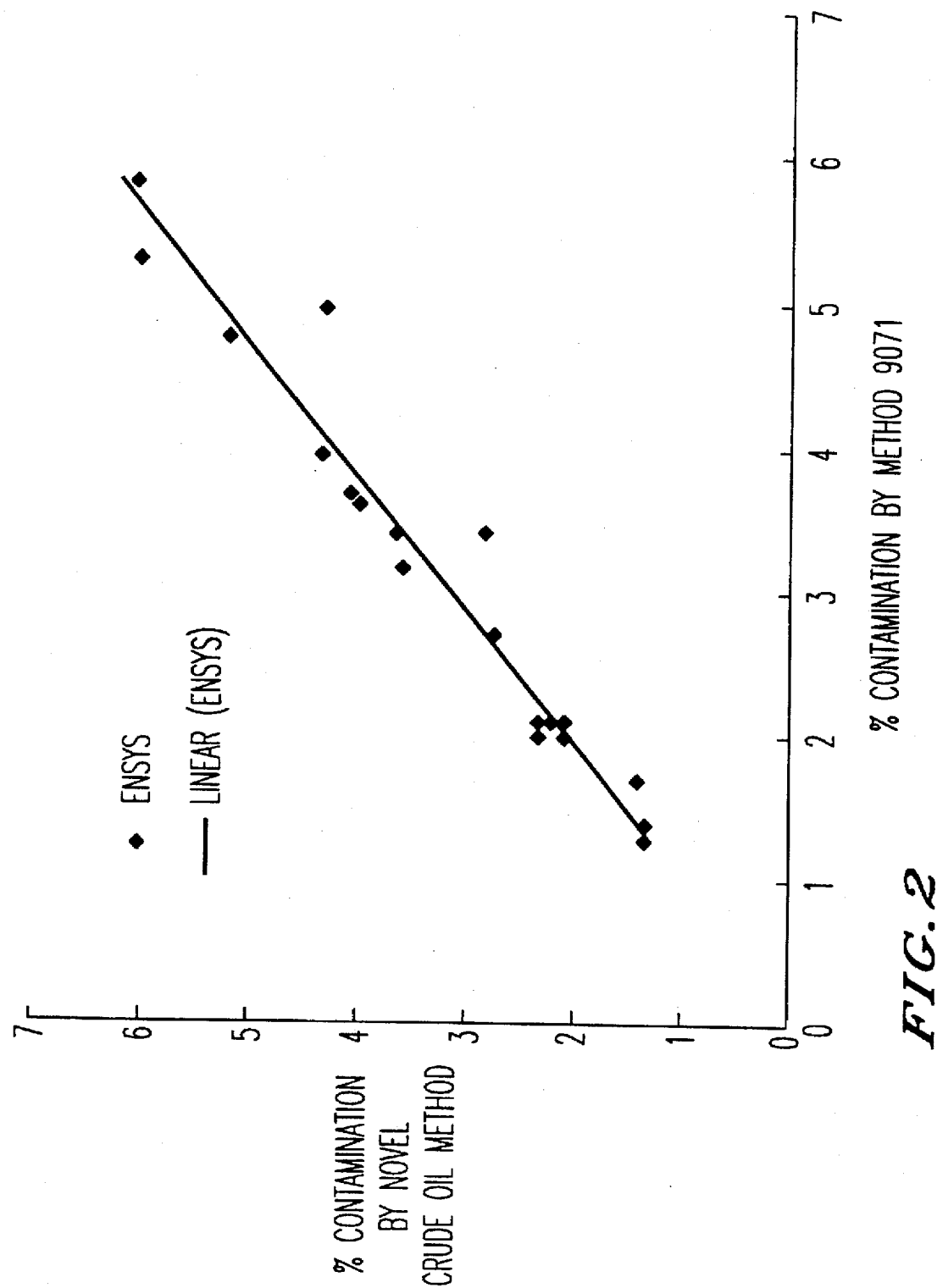
FIG. 2 is a graph showing the correlation of the present turbidimetric method for detecting crude oil with the conventional gravimetric method.

FIG. 2 shows the correlation between the conventional gravimetric method (EPA 9071) and the turbidimetric-derived value for contamination found in the present invention. As seen in FIG. 2 and the data of Table 2, at levels of contamination from 0.65–6% in soil, the present method gave a linear least squares correlation coefficient of 0.95 when compared with the conventional gravimetric method.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for the equivalent detection and quantitation of crude oil in a soil matrix, regardless of API number of the crude oil, consisting essentially of:
    (a) providing a particulate free extract of a dried soil sample suspected of containing crude oil by filtration of a suspension produced by admixing a soil sample with an oil dissolving water-miscible solvent in the presence of a drying agent, wherein said oil dissolving water-miscible solvent is a member selected from the group consisting of methanol, ethanol, propanol, isopropanol, 2-methoxyethyl alcohol, 2-ethoxyethyl alcohol, 3-ethoxy propanol, di(ethylene)glycol methylether, di(ethylene)glycol ethyl ether, di(propylene glycol), tri(ethylene glycol), poly(ethylene glycol)s, diglyme, dioxane, ethyleneglycol dimethyl ether, 1,2-dimethoxy propane and 2-ethoxyethyl ether;
    (b) dispersing the particulate free extract in an aqueous medium comprising: an emulsifier and water to prepare a stable aqueous emulsion;

(c) measuring turbidity of the stable aqueous emulsion; and (d) comparing the measured turbidity to a standard curve to obtain a concentration value for oil in the soil matrix, wherein the measured turbidity relates turbidity of the emulsion to crude oil concentration in the emulsion, regardless of crude oil composition or API number of the crude oil.

2. The method of claim 1, wherein said solvent is 2-methoxymethylether (diglyme).

3. The method of claim 1, wherein said emulsifier is a member selected from the group consisting of (HLB 13.5) alkylphenoxy polyethoxy ethanol, (HLB 14.6) octylphenoxy polyethoxy ethanol, (HLB 12.4) octylphenoxy polyethoxy ethanol, (HLB 10.4) octylphenoxy polyethoxy ethanol, (HLB 15.8) octylphenoxy polyethoxy ethanol, (HLB 16.7) POE (20) sorbitan monolaurate, (HLB 13.3) POE (4) sorbitan monolaurate, (HLB 14.9); POE (20) sorbitan monostearate, and (HLB 13.5) Linear synthetic alcohol ethoxylate.

4. The method of claim 3, wherein said emulsifier is (HLB 13.5) alkylphenoxy polyethoxy ethanol.

5. The method of claim 1, wherein said drying agent is a member selected from the group consisting of anhydrous sodium sulfate, 4 Å molecular sieves, anhydrous magnesium sulfate, anhydrous calcium sulfate, silica gel, alumina and phosphorous oxide.

6. The method of claim 5, wherein said drying agent is anhydrous magnesium sulfate.

7. The method of claim 1, wherein said emulsifier is a member selected from the group consisting of (HLB 13.5) alkylphenoxy polyethoxy ethanol, (HLB 14.6) octylphenoxy polyethoxy ethanol, (HLB 12.4) octylphenoxy polyethoxy ethanol, (HLB 10.4) octylphenoxy polyethoxy ethanol, (HLB 15.8) octylphenoxy polyethoxy ethanol, (HLB 16.7) POE (20) sorbitan monolaurate, (HLB 13.3) POE (4) sorbitan monolaurate, (HLB 14.9); POE (20) sorbitan monostearate, and (HLB 13.5) Linear synthetic alcohol ethoxylate.

8. The method of claim 7, wherein said emulsifier is (HLB 13.5) alkylphenoxy polyethoxy ethanol.

9. The method of claim 8, wherein said solvent is diglyme, said drying agent is anhydrous magnesium sulfate.

10. A method for the equivalent and quantitative determination of crude oil in a soil matrix, regardless of API number of the crude oil, consisting essentially of:

extracting a soil sample with a solvent in the presence of a drying agent to provide an extract containing oil, if present in said soil sample, wherein said solvent provides quantitative solvation of oil present in the soil sample and said solvent is completely miscible with water, wherein said solvent is a member selected from the group consisting of methanol, ethanol, propanol, isopropanol, 2-methoxyethyl alcohol, 2-ethoxyethyl alcohol, 3-ethoxy propanol, di(ethylene)glycol methylether, di(ethylene)glycol ethyl ether, di(propylene glycol), tri(ethylene glycol), poly (ethylene glycol)s, diglyme, dioxane, ethyleneglycol dimethyl ether, 1,2-dimethoxy propane and 2-ethoxyethyl ether;

filtering said extract;

combining said filtered extract with water in the presence of an emulsifier to form an assay sample; and determining the amount of crude oil in said soil sample by measuring turbidity of said assay sample to provide a turbidimetric response for said assay sample which correlates to concentration of crude oil present in said assay sample and is independent of crude oil composition or API number and comparing said turbidimetric response to a standard curve prepared from performing said extracting, filtering, combining and determining steps on soil samples of known crude oil content.

11. The method of claim 10, wherein said solvent is 2-methoxymethylether (diglyme).

12. The method of claim 10, wherein said emulsifier is a member selected from the group consisting of (HLB 13.5) alkylphenoxy polyethoxy ethanol, (HLB 14.6) octylphenoxy polyethoxy ethanol, (HLB 12.4) octylphenoxy polyethoxy ethanol, (HLB 10.4) octylphenoxy polyethoxy ethanol, (HLB 15.8) octylphenoxy polyethoxy ethanol, (HLB 16.7) POE (20) sorbitan monolaurate, (HLB 13.3) POE (4) sorbitan monolaurate, (HLB 14.9); POE (20) sorbitan monostearate, and (HLB 13.5) Linear synthetic alcohol ethoxylate.

13. The method of claim 12, wherein said emulsifier is (HLB 13.5) alkylphenoxy polyethoxy ethanol.

14. The method of claim 10, wherein said drying agent is a member selected from the group consisting of anhydrous sodium sulfate, 4 Å molecular sieves, anhydrous magnesium sulfate, anhydrous calcium sulfate, silica gel, alumina and phosphorous oxide.

15. The method of claim 14, wherein said drying agent is anhydrous magnesium sulfate.

16. The method of claim 10, wherein said emulsifier is a member selected from the group consisting of (HLB 13.5) alkylphenoxy polyethoxy ethanol, (HLB 14.6) octylphenoxy polyethoxy ethanol, (HLB 12.4) octylphenoxy polyethoxy ethanol, (HLB 10.4) octylphenoxy polyethoxy ethanol, (HLB 15.8) octylphenoxy polyethoxy ethanol, (HLB 16.7) POE (20) sorbitan monolaurate, (HLB 13.3) POE (4) sorbitan monolaurate, (HLB 14.9); POE (20) sorbitan monostearate, and (HLB 13.5) Linear synthetic alcohol ethoxylate.

17. The method of claim 16, wherein said emulsifier is (HLB 13.5) alkylphenoxy ethanol.

18. The method of claim 17, wherein said solvent is diglyme, and said drying agent is anhydrous magnesium sulfate.

* * * * *